US010187792B2

(12) United States Patent
Meskens

(10) Patent No.: US 10,187,792 B2
(45) Date of Patent: Jan. 22, 2019

(54) SECURE WIRELESS COMMUNICATION FOR AN IMPLANTABLE COMPONENT

(71) Applicant: Cochlear Limited, Macquarie University, NSW (AU)

(72) Inventor: Werner Meskens, Opwijk (BE)

(73) Assignee: Cochlear Limited, Macquarie University (AU)

( * ) Notice: Subject to any disclaimer, the term of this patent is extended or adjusted under 35 U.S.C. 154(b) by 45 days.

(21) Appl. No.: 15/362,952

(22) Filed: Nov. 29, 2016

(65) Prior Publication Data

US 2017/0161449 A1 Jun. 8, 2017

Related U.S. Application Data

(60) Provisional application No. 62/263,779, filed on Dec. 7, 2015.

(51) Int. Cl.

| | |
|---|---|
| ***A61N 1/372*** | (2006.01) |
| ***H04W 12/04*** | (2009.01) |
| ***H04W 12/06*** | (2009.01) |
| ***G16H 40/40*** | (2018.01) |
| ***G06F 19/00*** | (2018.01) |
| *H04W 12/02* | (2009.01) |
| *A61N 1/36* | (2006.01) |

(52) U.S. Cl.

CPC ........ *H04W 12/04* (2013.01); *A61N 1/37223* (2013.01); *A61N 1/37254* (2017.08); *G06F 19/00* (2013.01); *G16H 40/40* (2018.01); *H04W 12/06* (2013.01); *A61N 1/36038* (2017.08); *H04W 12/02* (2013.01)

(58) Field of Classification Search

CPC ............ A61N 1/37254; A61N 1/36036; A61N 1/37252

See application file for complete search history.

(56) References Cited

U.S. PATENT DOCUMENTS

| | | | | |
|---|---|---|---|---|
| 8,515,070 B2 | 8/2013 | Juels et al. | | |
| 2011/0015693 A1 | 1/2011 | Williamson | | |
| 2011/0159963 A1 | 6/2011 | Link | | |
| 2012/0003933 A1* | 1/2012 | Baker | H04W 76/38 | 455/41.2 |
| 2012/0116480 A1* | 5/2012 | Tsay | A61N 1/36036 | 607/57 |
| 2012/0266221 A1* | 10/2012 | Castelluccia | H04L 9/3271 | 726/6 |

(Continued)

OTHER PUBLICATIONS

Ali, et al., "A Bluetooth Low Energy Implantable Glucose Monitoring System," Proceedings of the 41st European Microwave Conference, Oct. 2011, 4 pages.

(Continued)

*Primary Examiner* — Kennedy Schaetzle

(74) *Attorney, Agent, or Firm* — Edell, Shapiro & Finnan, LLC

(57) ABSTRACT

Embodiments presented herein are generally directed to techniques for creation of a direct secured wireless link/channel between an implantable component and an external device of an implantable medical device system. More specifically, the implantable medical device system includes an external component that is configured to operate as a temporary secure proxy device for wireless pairing of the implantable component with the external device.

23 Claims, 7 Drawing Sheets

250

GENERATING A FIRST SET OF SECURITY DATA FOR FORMATION OF A SECURE NON-CLOSELY COUPLED CONNECTION BETWEEN AN EXTERNAL DEVICE AND AN EXTERNAL COMPONENT OF AN IMPLANTABLE MEDICAL DEVICE SYSTEM — 252

TRANSFERRING THE FIRST SET OF SECURITY DATA TO AN IMPLANTABLE COMPONENT OF THE IMPLANTABLE MEDICAL DEVICE SYSTEM — 254

AT THE IMPLANTABLE COMPONENT, USING THE FIRST SET OF SECURITY DATA TO IMITATE THE EXTERNAL COMPONENT FOR DIRECT COMMUNICATION WITH THE EXTERNAL DEVICE OVER THE SECURE NON-CLOSELY COUPLED CONNECTION — 256

(56) References Cited

U.S. PATENT DOCUMENTS

| | | | | |
|---|---|---|---|---|
| 2013/0045684 | A1 | 2/2013 | Linde et al. | |
| 2013/0247194 | A1 | 9/2013 | Jha et al. | |
| 2013/0265144 | A1 | 10/2013 | Banna et al. | |
| 2014/0273824 | A1 | 9/2014 | Fenner et al. | |
| 2016/0250490 | A1* | 9/2016 | Hoffman | A61N 1/37252 607/60 |
| 2017/0056677 | A1* | 3/2017 | Zhang | A61N 1/37211 |

OTHER PUBLICATIONS

Wikipedia, "Wireless Security," retrieved from https://en.wikipedia.org/w/index.php?title=Wireless_security&oldid=750145299, Nov. 2016, 15 pages.

Balmus, "Bluetooth Low Energy SMP Pairing," NXP Discussion, retrieved from https://community.freescale.com/message/442290#442290, Oct. 2014, 6 pages.

Wikipedia, "Bluetooth," Retrieved from https://en.wikipedia.org/w/index.php?title=Bluetooth&oldid=751027000, Nov. 2016, 22 pages.

"Bluetooth," Bluetooth SIG Proprietary Information, Technology Overview, retrieved from https://developer.bluetooth.org/TechnologyOverview/Pages/LE-Security.aspx, Nov. 2016, 5 pages.

BluegigaAdmin, "Bluetooth Pairing Machanism (Legacy Pairing and Secure Simple Pairing (SSP))," retrieved from http://community.silabs.com/t5/tkb/articleprintpage/tkb-id/BluetoothandWiFi%40tkb/article-id/106, Aug. 2015, 3 pages.

Rajan, "Enabling today's wireless medical devices, implants," retrieved from http://www.todaysmedicaldevelopments.com/article/medical-device-design-wireless-technology-1215/, Jan. 2015, 7 pages.

Sandhana, "Patients' own heartbeat could work as anti-hacking password for implants," retrieved from http://newatlas.com/password-for-medical-implants/29227/, Sep. 2013, 2 pages.

International Search Report and Written Opinion in counterpart International Application No. PCT/IB2016/057375, dated Mar. 15, 2017, 9 pages.

* cited by examiner

COCHLEAR IMPLANT
104
114
116
118
128
126
120
COCHLEAR IMPLANT
5MHz INDUCTIVE
RF CONNECTION
130
SKIN/TISSUE
101
112
108
HEADPIECE DEVICE
134
133
EXTERNAL DEVICE
106

COCHLEAR IMPLANT
104
114
126
128
118
116
174
STIMULATOR UNIT
180
BATTERY
172
SOUND PROCESSOR
170
NON-CLOSELY COUPLED TRANSCEIVER
178
CLOSELY COUPLED WIRELESS RECEIVER
176
MICROPHONE
182
RF COIL
101
SKIN/TISSUE

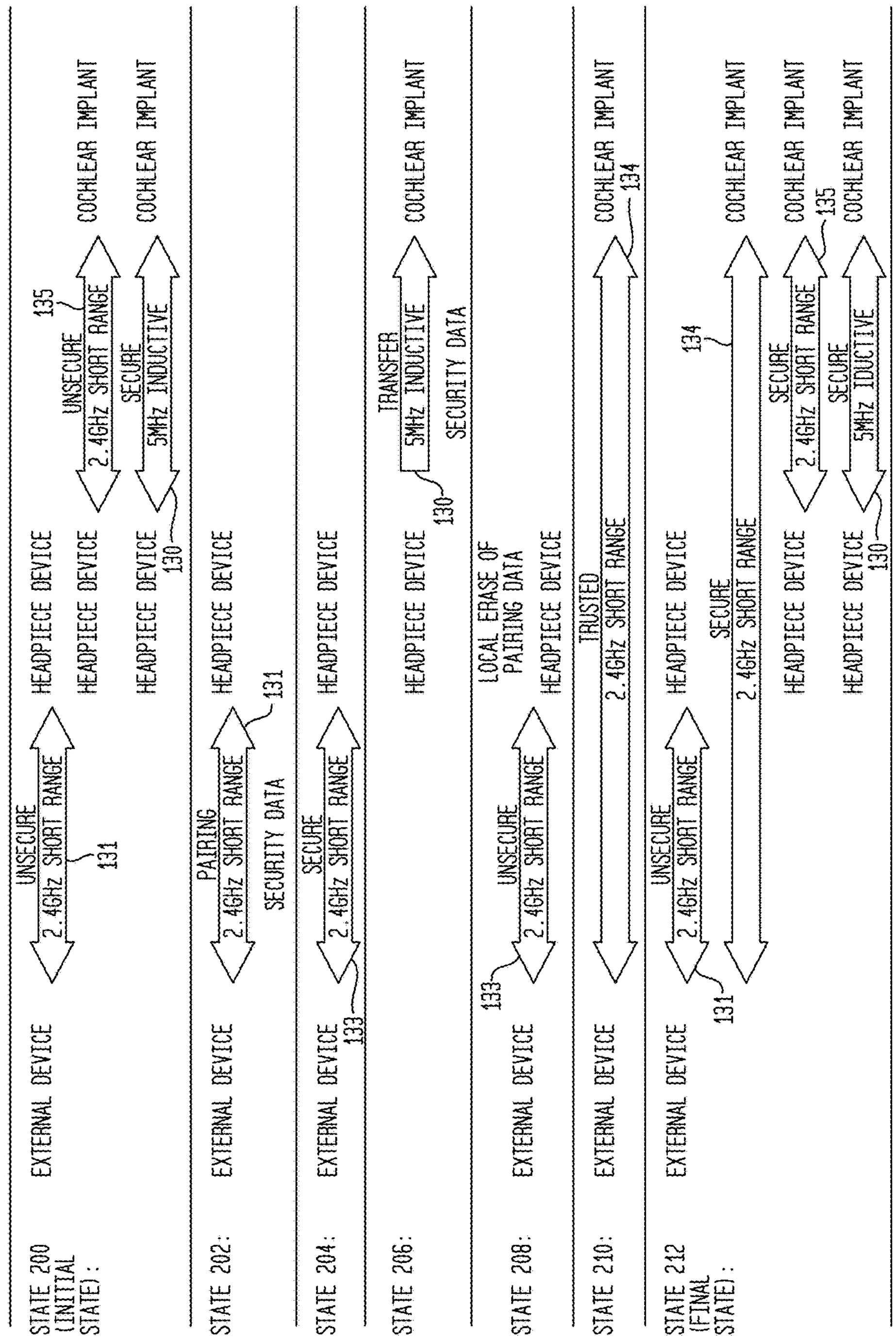
FIG. 5
STATE 200 (INITIAL STATE):
EXTERNAL DEVICE
UNSECURE
2.4GHz SHORT RANGE
131
HEADPIECE DEVICE
HEADPIECE DEVICE
UNSECURE
2.4GHz SHORT RANGE
135
COCHLEAR IMPLANT
HEADPIECE DEVICE
130
SECURE
5MHz INDUCTIVE
COCHLEAR IMPLANT
STATE 202:
EXTERNAL DEVICE
PAIRING
2.4GHz SHORT RANGE
SECURITY DATA
131
HEADPIECE DEVICE
STATE 204:
EXTERNAL DEVICE
133
SECURE
2.4GHz SHORT RANGE
HEADPIECE DEVICE
STATE 206:
HEADPIECE DEVICE
130
TRANSFER
5MHz INDUCTIVE
SECURITY DATA
COCHLEAR IMPLANT
STATE 208:
EXTERNAL DEVICE
133
UNSECURE
2.4GHz SHORT RANGE
LOCAL ERASE OF PAIRING DATA
HEADPIECE DEVICE
STATE 210:
EXTERNAL DEVICE
TRUSTED
2.4GHz SHORT RANGE
COCHLEAR IMPLANT
134
STATE 212 (FINAL STATE):
EXTERNAL DEVICE
UNSECURE
2.4GHz SHORT RANGE
131
HEADPIECE DEVICE
SECURE
2.4GHz SHORT RANGE
134
COCHLEAR IMPLANT
HEADPIECE DEVICE
SECURE
2.4GHz SHORT RANGE
135
COCHLEAR IMPLANT
HEADPIECE DEVICE
130
SECURE
5MHz IDUCTIVE
COCHLEAR IMPLANT

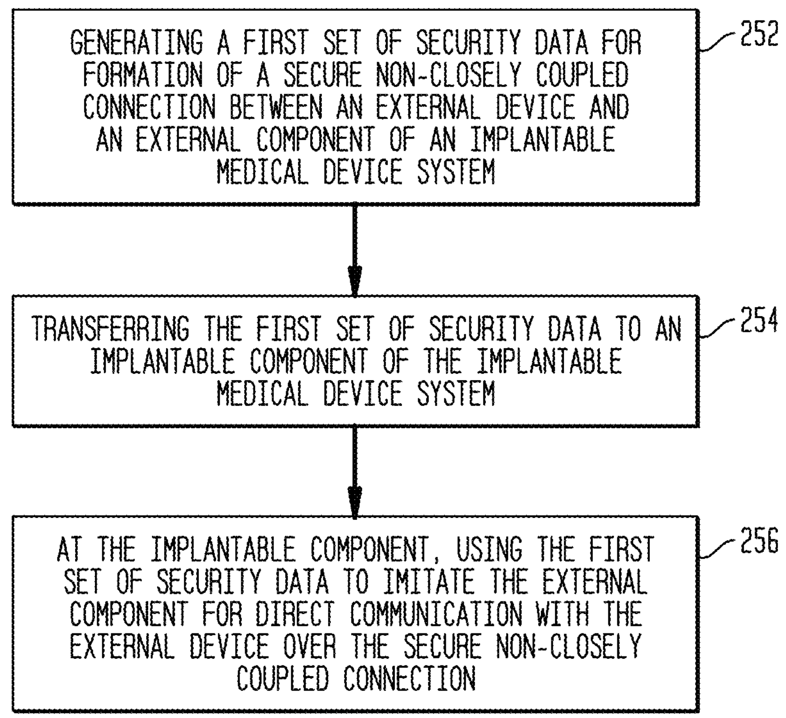
FIG. 7
250
GENERATING A FIRST SET OF SECURITY DATA FOR FORMATION OF A SECURE NON-CLOSELY COUPLED CONNECTION BETWEEN AN EXTERNAL DEVICE AND AN EXTERNAL COMPONENT OF AN IMPLANTABLE MEDICAL DEVICE SYSTEM
252
TRANSFERRING THE FIRST SET OF SECURITY DATA TO AN IMPLANTABLE COMPONENT OF THE IMPLANTABLE MEDICAL DEVICE SYSTEM
254
AT THE IMPLANTABLE COMPONENT, USING THE FIRST SET OF SECURITY DATA TO IMITATE THE EXTERNAL COMPONENT FOR DIRECT COMMUNICATION WITH THE EXTERNAL DEVICE OVER THE SECURE NON-CLOSELY COUPLED CONNECTION
256

SECURE WIRELESS COMMUNICATION FOR AN IMPLANTABLE COMPONENT

CROSS REFERENCE TO RELATED APPLICATIONS

This application claims priority to U.S. Provisional Application No. 62/263,779 entitled "Secure Wireless Communication for an Implantable Component," filed Dec. 7, 2015, the content of which is hereby incorporated by reference herein.

BACKGROUND

Field of the Invention

The present invention relates generally to wireless communications in implantable medical device systems.

Related Art

Implantable medical device systems, which include one or more implantable components, provide a wide range of therapeutic benefits to recipients. The types of implantable medical device systems and the ranges of functions performed thereby have increased over the years. For example, many implantable medical device systems now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify the anatomy or of a physiological process.

SUMMARY

In one aspect, an implantable medical device system is provided. The implantable medical device system comprises: an implantable component configured to be implanted in a recipient of the implantable medical device system; an external device; and an external component configured to be attached to the recipient and configured to operate as a temporary secure proxy device for wireless pairing of the implantable component with the external device.

In another aspect, a method is provided. The method comprises: generating a first set of security data for formation of a secure non-closely coupled connection between an external device and an external component of an implantable medical device system; transferring the first set of security data to an implantable component of the implantable medical device system; and at the implantable component, using the first set of security data to imitate the external component for direct communication with the external device over the secure non-closely coupled connection.

In another aspect an implantable medical device system is provided. The implantable medical device system comprises: an implantable component configured to be implanted in to a recipient of the implantable medical device system; and an external component having a first unique device address assigned thereto, wherein the external is configured to: use the first unique device address to wirelessly pair the external component with an external device and form a non-closely coupled wireless connection between the external component and the external device, and transfer the first address to the implantable component, wherein the implantable component is configured to use the first address to communicate with the external device on the non-closely coupled wireless connection formed between the external component and the external device.

BRIEF DESCRIPTION OF THE DRAWINGS

Embodiments of the present invention are described herein in conjunction with the accompanying drawings, in which:

FIG. 5 is a diagram illustrating successive connectivity states for components of a cochlear implant system in accordance with embodiments presented herein;

FIG. 7 is a flowchart of a method in accordance with embodiments presented herein.

DETAILED DESCRIPTION

Embodiments presented herein are generally directed to techniques for creation of a direct secured (trusted) wireless link/channel between an implantable component and an external device of an implantable medical device system. More specifically, as described further below, the implantable medical device system includes an external component/device that is configured to operate as a temporary secure proxy device to wireless pair the implantable component with the external device.

There are many types of implantable medical device systems that include one or more implantable components. However, merely for ease of illustration, the techniques presented herein are primarily described herein with reference to one type of implantable medical device system, namely a cochlear implant system. It is to be appreciated that the techniques presented herein may be used with other implantable medical device systems that include, for example, auditory brainstem stimulator systems, implantable pacemaker systems, defibrillator systems, functional electrical stimulation systems, pain relief stimulator systems, visual prosthesis systems, implantable sensor systems, and/or other systems having functional implantable components configured to diagnosis, prevent, monitor, treat or manage a disease or injury or symptom thereof, or configured to investigate, replace or modify the anatomy or of a physiological process.

Figure 1:
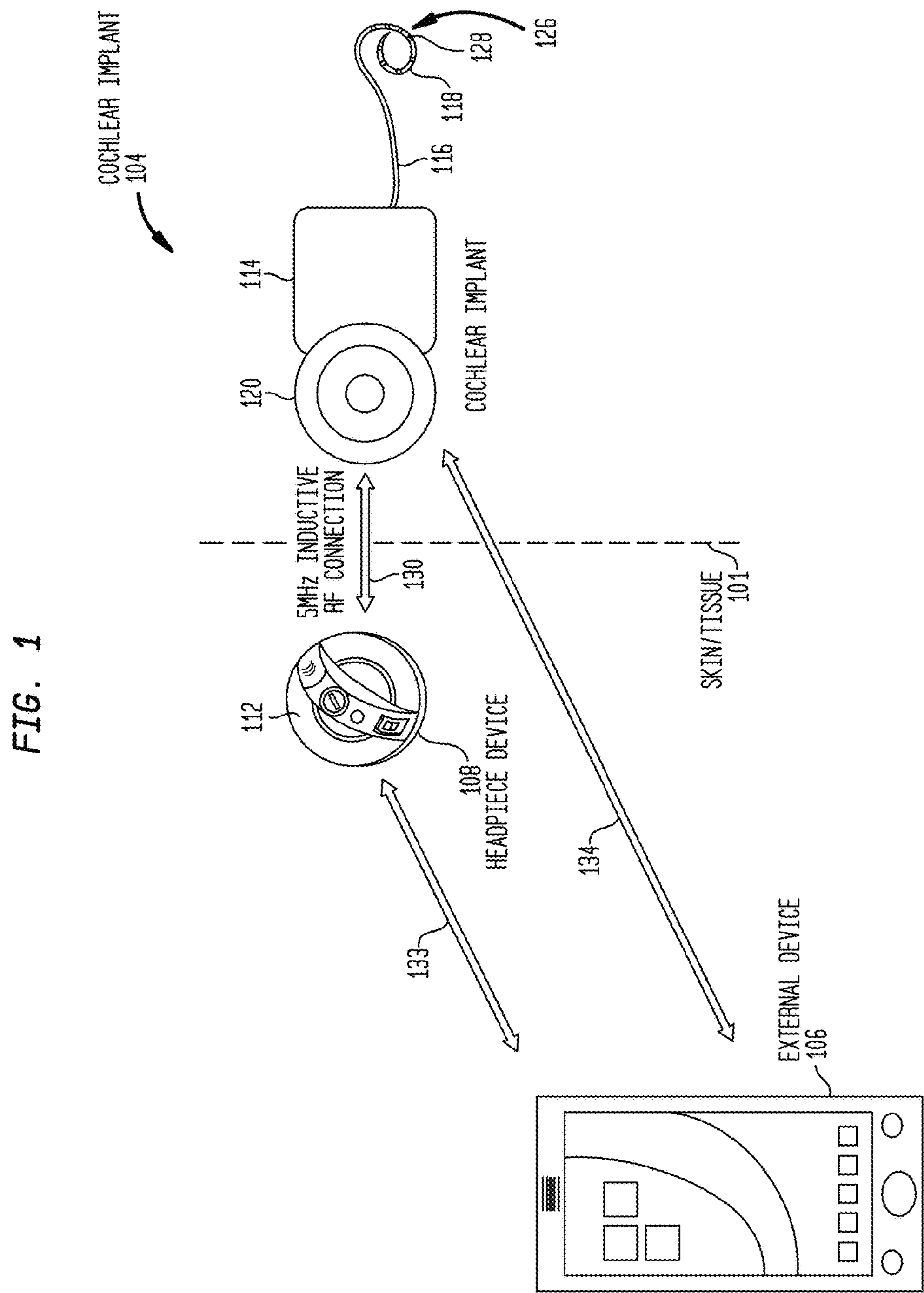
FIG. 1 is a schematic diagram illustrating a cochlear implant system in accordance with embodiments presented herein.

FIG. 1 is schematic diagram of an exemplary cochlear implant system 100 configured to implement embodiments of the present invention. As shown, the cochlear implant system 100 comprises an external device 106, an external component (headpiece device) 108 configured to be attached to a recipient, and an implantable component 104 configured to be implanted under the skin/tissue 101 of the recipient. In this example, the implantable component 104 is a cochlear implant and the external component is a headpiece device that is configured to be attached to the head of a recipient.

Figure 2:
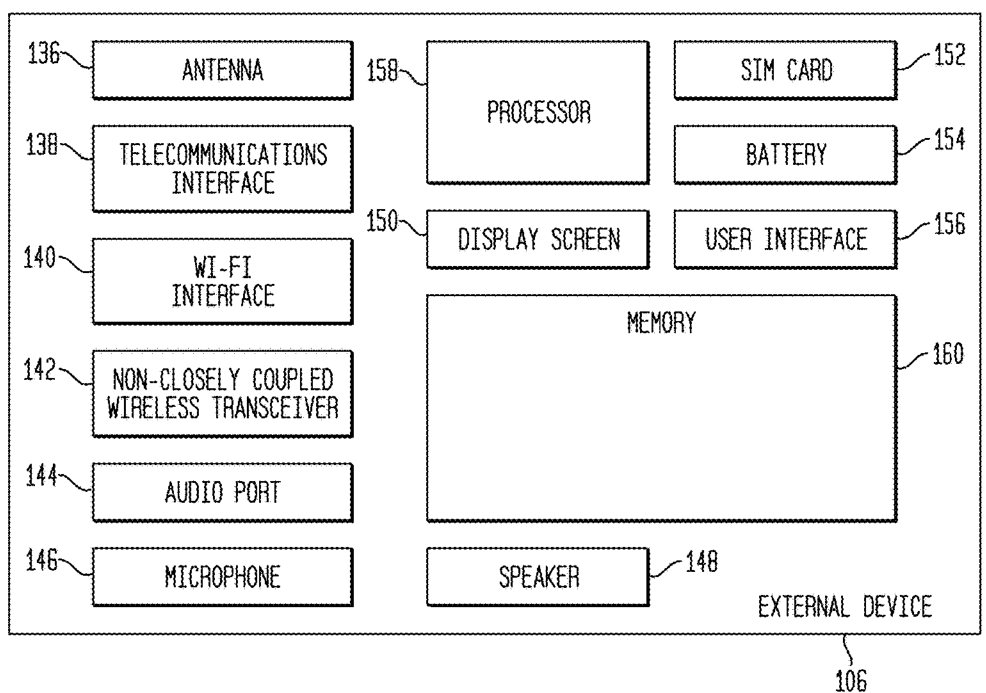
FIG. 2 is a block diagram of an external device of a cochlear implant system in accordance with embodiments presented herein.
Figure 3:
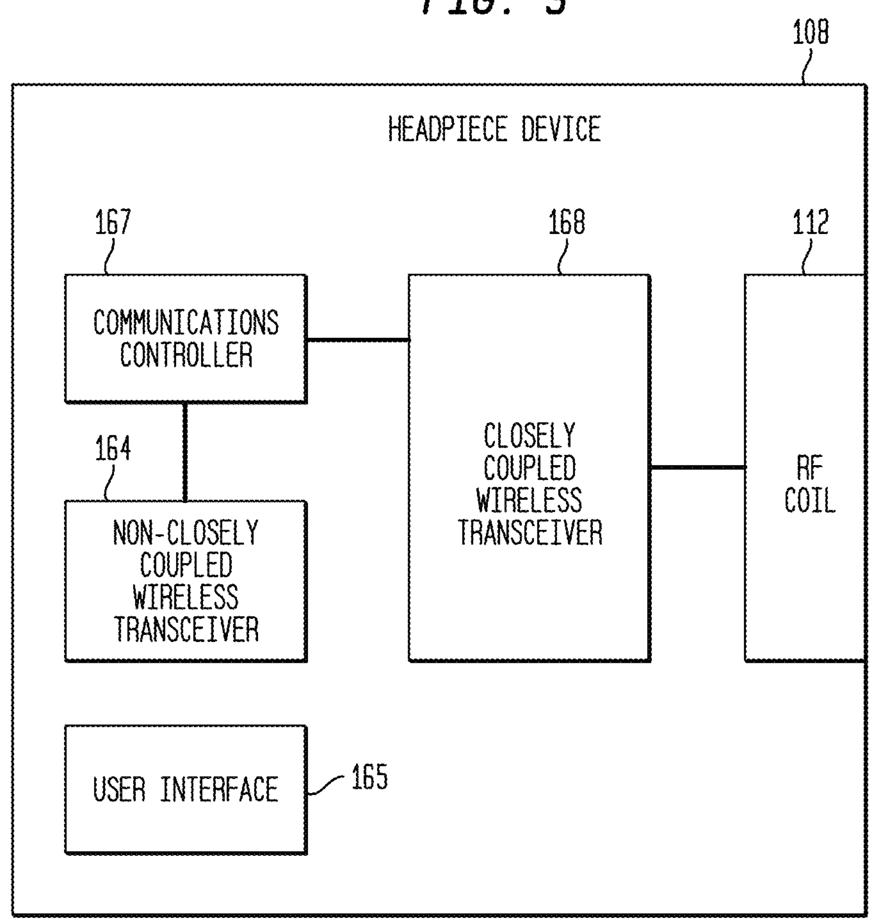
FIG. 3 is a block diagram of a headpiece device of a cochlear implant system in accordance with embodiments presented herein.
Figure 4:
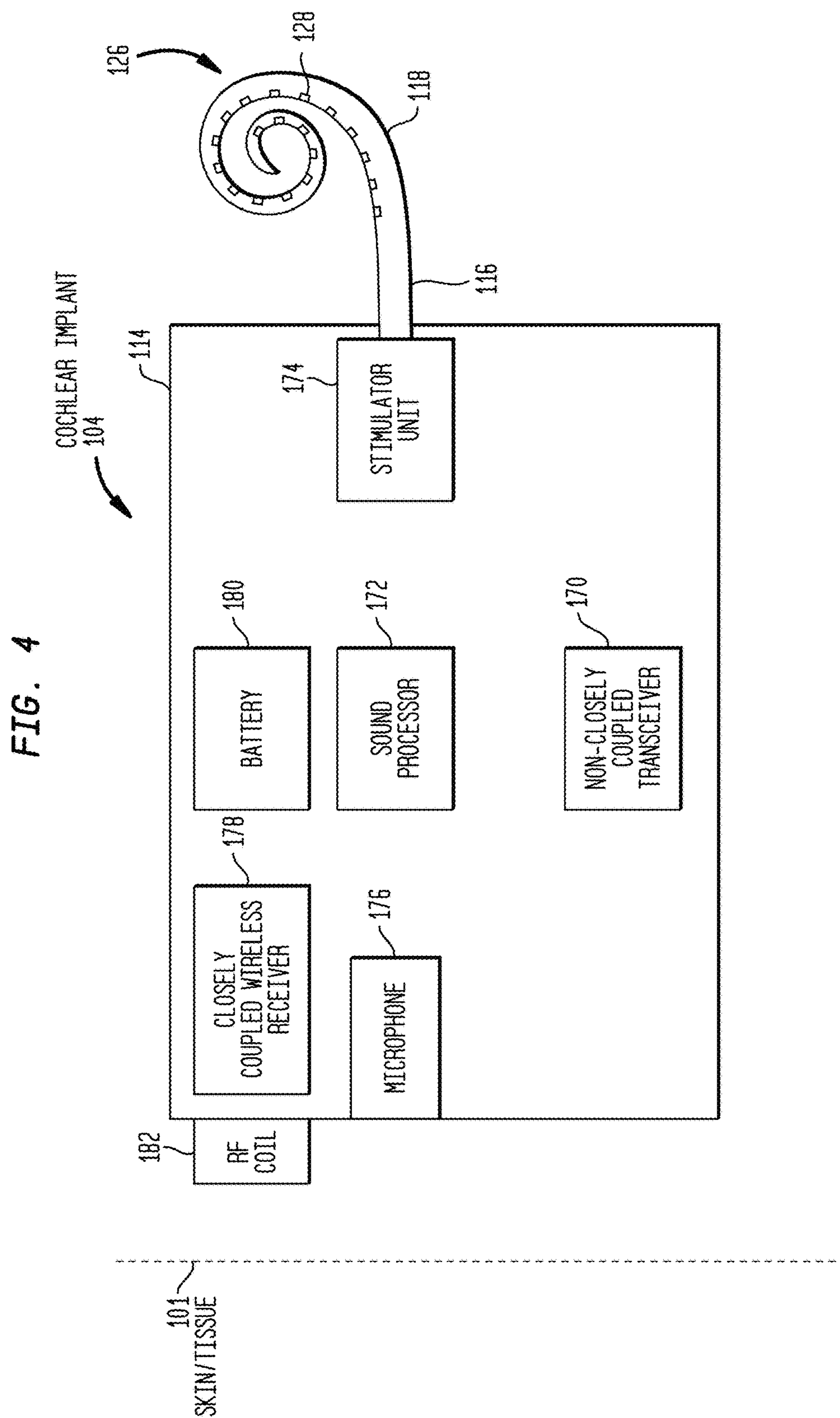
FIG. 4 is a block diagram of an implantable component of a cochlear implant system in accordance with embodiments presented herein.

Further details of the external device 106 are shown in FIG. 2, further details of the headpiece device 108 are shown in FIG. 3, and further details of the cochlear implant 104 are shown in FIG. 4.

As described further below, the external device 106, headpiece device 108, and cochlear implant 104 all include a wireless transceiver configured for wireless communication in accordance with a non-closely coupled short-range wireless standard (i.e., over non-closely coupled wireless link/connection). Wireless transceivers configured for wireless communication over a non-closely coupled wireless connection are referred to herein as non-closely coupled wireless transceivers. In certain embodiments, the non-closely coupled wireless transceivers are Bluetooth® transceivers that communicate using short-wavelength Ultra High Frequency (UHF) radio waves in the industrial, scientific and medical (ISM) band from 2.4 to 2.485 gigahertz (GHz). Bluetooth® is a registered trademark owned by the Bluetooth® SIG.

The external device 106 may be, for example, a remote control device (remote control), a smartphone, or other device that is useable to change settings of other devices. In addition to the non-closely coupled wireless transceiver, the headpiece device 108 further comprises an external RF coil 112, a magnet fixed relative to the external coil, and a second wireless transceiver configured for communication with cochlear implant 104 over a closely coupled radio frequency (RF) link 130 (e.g., a 5 megahertz (MHz) inductive RF link). FIG. 1 illustrates an example in which the headpiece device 108 is a component having a generally cylindrical shape and which is configured to be magnetically coupled to the recipient's head, sometimes referred to herein as a "button" device. However, it is to be appreciated that the headpiece device 108 could alternatively be a behind-the-ear (BTE) unit, such as a mini or micro-BTE, configured to be attached to and worn adjacent to the recipient's ear, or an in-the-canal unit that is configured to be located in the recipient's ear canal, etc.

The cochlear implant 104 comprises an implant body 114, in which the associated non-closely coupled wireless transceiver is positioned, a lead region 116, and an elongate intra-cochlear stimulating assembly 118. Cochlear implant 104 also comprises an internal RF coil 120, a magnet fixed relative to the internal coil, a stimulator unit, and a closely coupled wireless transceiver positioned in the implant body 114.

The magnets in the headpiece device 108 and the implant body 114 facilitate the operational alignment of the external coil 112 in the headpiece device with the internal coil 120 in the implant body. The operational alignment of the coils 112 and 120 enables the internal coil to trancutaneously receive power and data from the external coil over the closely-coupled RF link 130. The external and internal coils 112 and 120 are typically wire antenna coils.

Elongate stimulating assembly 118 is configured to be at least partially implanted in the cochlea of a recipient and includes a plurality of intra-cochlear stimulating contacts 128. The stimulating contacts 128 collectively form a contact array 126 and may comprise electrical contacts and/or optical contacts. Stimulating assembly 118 extends through an opening in the cochlea (e.g., cochleostomy, the round window, etc.) and has a proximal end connected to the stimulator unit in implant body 114 via lead region 116 that extends through the recipient's mastoid bone.

The use of smartphones, remote controls, and other consumer electronic devices is widespread and such devices are increasingly become integral to the daily routines of many individuals. As such, it may be desirable to enable a recipient of an implantable medical device system, such as a recipient of a cochlear implant system, to wirelessly control settings of the implantable medical device system using a smartphone, remote control, or other device. In conventional arrangements, direct wireless control of an implantable medical device system has been limited to external components only (i.e., no control over implantable components). The reason that control over implantable components has been limited is that current techniques are unable to properly secure the wireless connection between an external device and an implantable component.

More specifically, in order to enable control over a component of an implantable medical device system, the wireless connection between the control entity (controller) and the component should be secured. A secured wireless connection/link is needed to, for example: (1) prevent eavesdropping/disclosure threats (i.e., leaking of information from a system to an unwanted party), (2) prevent integrity threats (i.e., man-in-the-middle (MITM) protection against unauthorized changes to information during transmission), (3) prevent denial of service threats (i.e., blocking of resources by malicious attacker), or to protect against other types of threats. MITM attacks, in particular, occur when the attacker has the ability to both monitor and alter or inject messages into a communication channel. For example, in active eavesdropping techniques, the attacker makes independent connections with the devices at both ends of the connection and relays messages between them to make the devices believe they are talking directly to each other over a private connection, when in fact the entire conversation is controlled by the attacker. In such attacks, the attacker intercepts all relevant messages passing between the two victim devices and has the ability to inject new messages into the channel. If an MITM attack were to occur in an implantable medical device system, the attacker would effectively have control over the implantable component.

In wireless communication, a wireless connection between two devices can exist in both unsecure (untrusted) and secure (trusted) states. In an unsecure connection, the messages exchanged between the two devices can be processed by any device within the wireless range of the transmitting device. In a secure connection, the messages can only be decrypted by the intended device (i.e., the messages are encrypted for the intended device only). A wireless connection between two devices is generally secured through a pairing process (pairing) implemented by the communicating devices. Pairing generally results in authentication authorization, and symmetric key security (i.e., shared encryption/decryption keys). Authentication is the process of determining the identity of another device, while authorization is the process of deciding if device A has the access rights to device B. As used herein, a pairing process that results in MITM protection is referred to as an "authenticated pairing" process or simply "authenticated pairing."

There are a number of techniques for the wireless pairing of two devices with one another. However, these pairing techniques generally require user interaction at both of the devices being paired, particularly in the cases of authenticated pairing (i.e., where MITM protection is enabled). For example, users are typically required to enter codes, passwords, or other inputs to, for example, verify the validity of the connection, confirm that the correct devices are being paired (i.e., prevent erroneous pairing with a different device located within the same proximity), etc. However, in the specific context of implantable medical device systems, implantable components are surgically implanted within (inside) a recipient. Accordingly, these implantable components do not include user interfaces (i.e., buttons, displays, etc.) and are not accessible so as to enable user interaction therewith. As such, traditional pairing techniques requiring user inputs at both devices cannot be used for authenticated pairing (i.e., to create a secured wireless connection that also provides MITM protection between an external device and an implantable component).

Presented herein are techniques for authenticated pairing of an external device with an implantable component through an intermediate external device that is inherently trusted by the implantable component (i.e., create a secured wireless connection/link directly between an external device and an implantable component in a manner that provides MITM protection).

Referring first to the arrangement of FIG. 1, the headpiece device 108 operates as a temporary secure proxy device for authenticated pairing of the cochlear implant 104 with the external device 106. More specifically, the headpiece device forms a temporary non-closely coupled secured wireless communication connection/link 133 (referred to herein simply as a secured wireless connection) between itself and the external device 106. The headpiece device 108 then transfers, to the cochlear implant 104, all security related parameters and data (e.g., encryption/decryption keys, serial number exchange, Media Access Control (MAC) address) received/negotiated with the external device 106. The security related parameters and data are transferred to the cochlear implant 104 over the closely coupled inductive RF link 130.

Once the transfer of the security related parameters and data is complete, the cochlear implant 104 is configured to imitate the secured wireless connection 133 of the headpiece device 108. In other words, using the security data received from the headpiece device 108, the cochlear implant 104 securely spoofs the connection 133 formed between the external device 106 and the headpiece device 108 so as to enable a secured wireless connection 134 directly between the cochlear implant and the external device. The cochlear implant 104 is referred to as "imitating" or "spoofing" the secured wireless connection 133 because, from the view of the external device 106, the connection has not changed. In other words, the external device 106 continues to believe it is communicating with the headpiece device 108, while in fact it is communicating directly with the cochlear implant 104.

Before further describing the techniques presented herein for forming a secure wireless connection between the cochlear implant 104 and the external device 106, further details of the external device 106, headpiece device 108, and cochlear implant 104 are first provided with reference to FIGS. 2, 3, and 4, respectively.

More specifically, FIG. 2 is a block diagram of an arrangement in which the external device 106 is a smartphone. It is to be appreciated that FIG. 2 is merely illustrative and that external device 106 is not limited to the example arrangement shown in FIG. 2.

External device 106 first comprises an antenna 136 and a telecommunications interface 138 (e.g., a wide area network (WAN) interface, such as a GSM, EG, ISM, LTE, etc. interface) that are configured for communication on a telecommunications network.

As shown in FIG. 2, external device 106 also includes a wireless local area network interface 140 and a non-closely coupled wireless interface/transceiver 142 (e.g., an infrared (IR) or Bluetooth® transceiver). The wireless local area network interface 140 allows the external device 106 to connect to the Internet, while the non-closely coupled wireless transceiver 142 enables the external device 106 to wirelessly communicate (i.e., directly receive and transmit data to/from another device via a wireless connection), such as over a 2.4 Gigahertz (GHz) link. As described further below, the non-closely coupled wireless transceiver 142 is used to wirelessly connect the external device 106 to both the headpiece device 108 and the cochlear implant 104. It is to be appreciated that that any other interfaces now known or later developed including, but not limited to, Institute of Electrical and Electronics Engineers (IEEE) 802.11, IEEE 802.16 (WiMAX), fixed line, Long Term Evolution (LTE), etc., may also or alternatively form part of the external device 106.

External device 106 also comprises an audio port 144, one or more sound input elements, such as a microphone 146, a speaker 148, a display screen 150, a subscriber identity module or subscriber identification module (SIM) card 152, a battery 154, a user interface 156, a processor 158, and a memory 160. The display screen 150 is an output device, such as a liquid crystal display (LCD), for presentation of visual information to the cochlear implant recipient. The user interface 156 may take many different forms and may include, for example, a keypad, keyboard, mouse, touchscreen, display screen, etc. Memory 160 may comprise any one or more of read only memory (ROM), random access memory (RAM), magnetic disk storage media devices, optical storage media devices, flash memory devices, electrical, optical, or other physical/tangible memory storage devices. The processor 158 is, for example, a microprocessor or microcontroller that executes instructions for the logic stored in memory 160.

FIG. 3 is a functional block diagram illustrating elements of headpiece device 108 in accordance with an example embodiment. Shown in FIG. 3 is a non-closely coupled wireless transceiver 164, a closely coupled wireless transceiver (i.e., RF encoder/coil driver) 168, the RF coil 112, a communications controller 167 controlling transfers, and a user interface 165 that includes at least one user input device (e.g., push button) and, optionally a display (e.g., numerical display). In general, FIG. 3 primarily illustrates the elements of the headpiece device 108 related to the receipt of data over a non-closely coupled wireless link and the transmission of data over a closely coupled wireless link. Other elements that may be included in the headpiece device 108 (e.g., batteries, magnet, microphone(s), sound processor, etc.), have been omitted from FIG. 3 for ease of illustration.

FIG. 4 is a functional block diagram of cochlear implant 104 configured to implement embodiments of the present invention. In this example, the cochlear implant 104 is a totally implantable cochlear implant where all components of the cochlear implant are configured to be implanted under skin/tissue 101 of the recipient. Because all components of cochlear implant 104 are implantable, the cochlear implant is configured to operate, for at least a finite period of time, without the need of headpiece device 108 and/or external device 106.

As noted above, cochlear implant 104 includes an implant body (main implantable component) 114, a lead region 116, and an elongate intra-cochlear stimulating assembly 118. Disposed in the implant body 114 are a non-closely coupled wireless transceiver 170, a sound processor 172, a stimulator unit 174, an implantable microphone 176, a closely coupled wireless receiver or transceiver 178, and a rechargeable battery 180, such as an integrated or removable lithium-ion (LiIon) battery. Operably connected to the RF transceiver

178 is an RF coil 182 that may be attached to the implant body 114. It is to be appreciated that, in certain examples, the RF transceiver 178 may be an RF receiver (i.e., no transmit functionality). However, merely for ease of illustration, examples are described herein with reference to the use of an RF transceiver 178

The implantable microphone 176 may be disposed in, or electrically connected to, the implant body 114. The sound processor 172 is configured to execute sound processing and coding to convert received/detected sound signals (e.g., received by microphone 178) into processed sound signals.

The closely coupled wireless transceiver 178 is configured to transcutaneously receive power and/or data from headpiece device 108 via the closely coupled RF link 130 (FIG. 1). As used herein, closely coupled wireless communication refers to communications that require close proximity between the communicating transceivers. In one specific example, closely coupled communication refers to communication between transceivers that are within approximately ten (10) centimeters (cm) of one another and/or are inductively coupled to one another. Although FIGS. 1, 3, and 4 illustrate the use of an RF link, it is to be appreciated that alternative embodiments may use other types of closely coupled links (e.g., infrared (IR), capacitive, etc.).

FIG. 5 is a diagram illustrating successive connectivity states of components of an implantable medical device system when forming a secured wireless connection between an external device and an implantable component in accordance with embodiments presented herein. For ease of illustration, FIG. 5 will be described with reference to the cochlear implant system 100 of FIGS. 1-4

FIG. 5 first illustrates, at reference number 200, an initial connectivity state for the components of the cochlear implant system 100. In the initial state 200, external device 106 and headpiece device 108 have an unsecure non-closely coupled wireless connection (e.g., a 2.4 GHz link) 131 formed there between. Similarly, headpiece device 108 may have both an unsecure non-closely coupled wireless connection 135 and a secure closely coupled wireless connection 130 (e.g., 5 MHz inductive link) with the cochlear implant 104.

The closely coupled wireless connection 130 is an "always trusted" or "always secure" connection due to the extremely short range nature of the RF signals, thereby requiring a close proximity (e.g., approximately 10 cm) between the headpiece device 108 and the cochlear implant 104. In other words, the closely coupled link 130 is considered secure because it is only susceptible to security threats when an attacker device is within the 10 cm proximity, which would be noticeable to the recipient or other user.

FIG. 5 illustrates, at reference number 202, a second connectivity state for the components of the cochlear implant system 100. In the state 202, the external device 106 and the headpiece device 108 perform aspects of an authenticated pairing process to convert the unsecure non-closely coupled wireless connection 131 into a secure non-closely coupled wireless connection 133 that provides MITM protection. Since both the external device 106 and the headpiece device 108 have user interfaces (i.e., at least one user input and optionally a display) substantially any pairing technique that provides MITM protection (e.g., numeric comparison, passkey Entry, Out of band (OOB), Near Field Communication (NFC), proximity pairing, accelerometer, etc.), may be used for the authenticated pairing of the headpiece device with the external device.

Although the specific pairing process implemented by the external device 106 and the headpiece device 108 may take a number of different forms, a pairing process generally involves the exchange of identity information between the devices so as to create a "trust" relationship and to determine encryption keys for future data exchange. For example, pairing generally includes several key pieces of information, including a PIN, a unique device address (e.g., a Bluetooth® device address (BD_ADR)), Private Authentication Keys, or Link Keys, a Private Encryption Key, and a RAND. The PIN is a number (typically up to 128 bits in length) that is entered into one or both of the devices. A Bluetooth® device address is a unique 48 bit sequence, where the first 24 bits are assigned by the Institute of Electrical and Electronics Engineers (IEEE) and the second 24 bits are assigned by the device manufacturer. In general, a device is required to know the unique device address (e.g., Bluetooth® device address) of the device with which it is to communicate. The Private Authentication Keys or Link Keys are 128-bit random numbers used for authentication purposes. Paired devices share a link key. The Private Encryption Key is a key of varying length (8-128 bits) that is regenerated for each transmission from the link key. The RAND is a frequently changing 128-bit random number generated by the device (in software).

Authenticated pairing may generally be divided into three steps, including: (1) an exchange of pairing information, (2) authentication of the link, and (3) distribution of the keys. The exchange of pairing information between two devices is done through "Pairing Request" and "Pairing Response" messages. The authentication step is performed based on the information exchanged in the Pairing Request and Pairing Response messages. In this step, a temporary key is generated which may be used by the devices to generate a Short-Term Key (STK). In the third phase of the pairing procedure, keys are distributed using specific packets. The distributed keys are encrypted with the STK. The RAND and the BD ADDR of the devices are also distributed in this phase.

The unique device address (e.g., a Bluetooth® device address (BD_ADR)), Private Authentication Keys, or Link Keys, a Private Encryption Key, RAND and other information, is collectively and generally referred to herein as "security data." Negotiation (i.e., generation, receipt, etc.) of the security data by the external device 106 and the headpiece device 108 results in the authenticated pairing of the external device and the headpiece device (i.e., the formation of the secure non-closely coupled wireless connection 133 there between with MITM protection). This is shown in FIG. 5 as a third connectivity state 204.

FIG. 5 illustrates, at reference number 206, a fourth connectivity state for the components of the cochlear implant system 100. In the state 206, the headpiece device 108 uses the always trusted closely coupled wireless connection 130 to transfer the security data negotiated with the external device 106 to the cochlear implant 104. In general, the security data transferred to the cochlear implant 104 includes all of security related parameters and data, including keys, serial numbers, etc., that is needed by the cochlear implant 104 to imitate the secure non-closely coupled wireless connection 133. Stated differently, the security data transferred in state 206 is all of the information that will by used by the cochlear implant 104 to securely communicate with the external device 106. Since, from the perspective of the cochlear implant 104, the headpiece device 108 is an inherently trusted device when communicating over the closely-coupled link, the cochlear implant 104 trusts the validity of received security data.

In one example, the pairing process is performed while the headpiece device 108 is decoupled from the recipient's head so that the user can easily manipulate the user interface 165 of the headpiece device. In certain such embodiments, the headpiece device 108 is configured to automatically transfer the security data to cochlear implant 104 when the headpiece device 108 is connected to the cochlear implant via the closely coupled wireless connection 130. However, in other embodiments, the headpiece device 108 may be configured to transfer the security data to cochlear implant 104 in response to a voice command, a user input at the headpiece device, etc. Furthermore, the headpiece device 108 may be configured to transfer the security data to the cochlear implant 104 using a low power communication mode (i.e., whisper mode) to further minimize the range in which the security data could be heard and captured by unintended devices.

Reference number 208 illustrates a fifth connectivity state in which, after all of the security data is transferred to the cochlear implant 104, the headpiece device 108 locally deletes/erases the security data previously negotiated with the external device 106. By locally deleting the security data, the headpiece device 108 essentially removes itself from the secure non-closely coupled wireless connection 133. That is, following the local deletion of the security data, the headpiece device 108 no longer has the ability to send information to the external device 106 in a secure manner and the headpiece device 108 will ignore any secured information that it received from the external device 106.

The cochlear implant 104 locally stores and processes the security data received from the headpiece device 108 so as to emulate operation of the headpiece device 108 in regards to the non-closely coupled wireless connection 133 (i.e., replaces headpiece device 108 at the end of the secure non-closely coupled wireless connection 133). That is, following receipt and processing of the security data, the cochlear implant 104 is able to securely transmit data to the external device 106 using the credentials/information negotiated between external device 106 and headpiece device 108. Similarly, the cochlear implant 104 is able to decode data transmitted by the external device 106 over connection 133.

Since cochlear implant 104 uses the security data that was negotiated between external device 106 and headpiece device 108, the connection between the cochlear implant and the external device is the same, from a security perspective, as the non-closely coupled wireless connection 133. However, merely for ease of description, the direct non-closely coupled wireless connection between cochlear implant 104 and external device 106 is referred to as non-closely coupled wireless connection 134.

Reference number 210 of FIG. 5 illustrates a sixth connectivity state where non-closely coupled wireless connection 134 has been formed between the external device 106 and the cochlear implant 104. In this state, the transceiver 142 of the external device 106 believes that it is communicating with the headpiece device 108. However, it should be appreciated that upper level functions of the external device 106 are aware that the non-closely coupled wireless connection 133 has been spoofed and that communications on connection 134 are in fact between the external device 106 and the cochlear implant 104.

Reference number 212 illustrates a final connectivity state for the components of the cochlear implant system 100. In the state 212, external device 106 and headpiece device 108 have the original unsecure non-closely coupled wireless connection 131 formed there between. Similarly, headpiece device 108 has both an unsecure non-closely coupled wireless connection 135 and a trusted closely coupled wireless connection 130 with the cochlear implant 104. Finally, external device 106 and the cochlear implant 104 have the secure non-closely coupled wireless connection 134 formed there between. As a result, the cochlear implant 104 has been paired with the external device 106 via the headpiece device 108.

In the final connectivity state 212, the external device 106 and the headpiece device 108 share only an unsecure non-closely coupled wireless connection 133. However, if there is a need for the external device 106 to securely communicate with the headpiece device 108, in accordance with embodiments presented herein the cochlear implant 104 may be configured to operate as a secure bridge/router device for the headpiece device. More specifically, the external device 106 may first transmit data intended for the headpiece device 108 to the cochlear implant 104 using the secure non-closely coupled wireless connection 134. Upon receipt of the data intended for the headpiece device 108, the cochlear implant 104 is configured to forward the data to the headpiece device using the inherently secure closely-coupled connection 130.

It is to be appreciated that the order of the connectivity states 200-212 shown in FIG. 5 are merely illustrative and, in certain examples, the order of connectivity states may vary. For example, in an alternative embodiment, connectivity state 210 may proceed connectivity state 208 such that the non-closely coupled wireless connection 134 is activated and confirmed before the headpiece device 108 deletes the security data. In one such example, the cochlear implant 104 transmits a message/notification to headpiece device 108 indicating that non-closely coupled wireless connection 134 has been successfully activated and that the headpiece device 108 may then delete the security data in response to receipt of this message. This process may operate as a safety mechanism in case the cochlear implant 104 needs the security data to be re-sent (i.e., if one or more initial attempts to activate non-closely coupled wireless connection 134 were unsuccessful).

Furthermore, it is to be appreciated that the connectivity states shown in FIG. 5 are illustrative and that additional states may be added and/or the connectivity states shown in FIG. 5 may be adjusted. For example, FIG. 6 is a diagram illustrating an alternative set of connectivity states for the components of cochlear implant system 100 when forming a secured wireless connection between external device 106 and cochlear implant 104.

Figure 6:
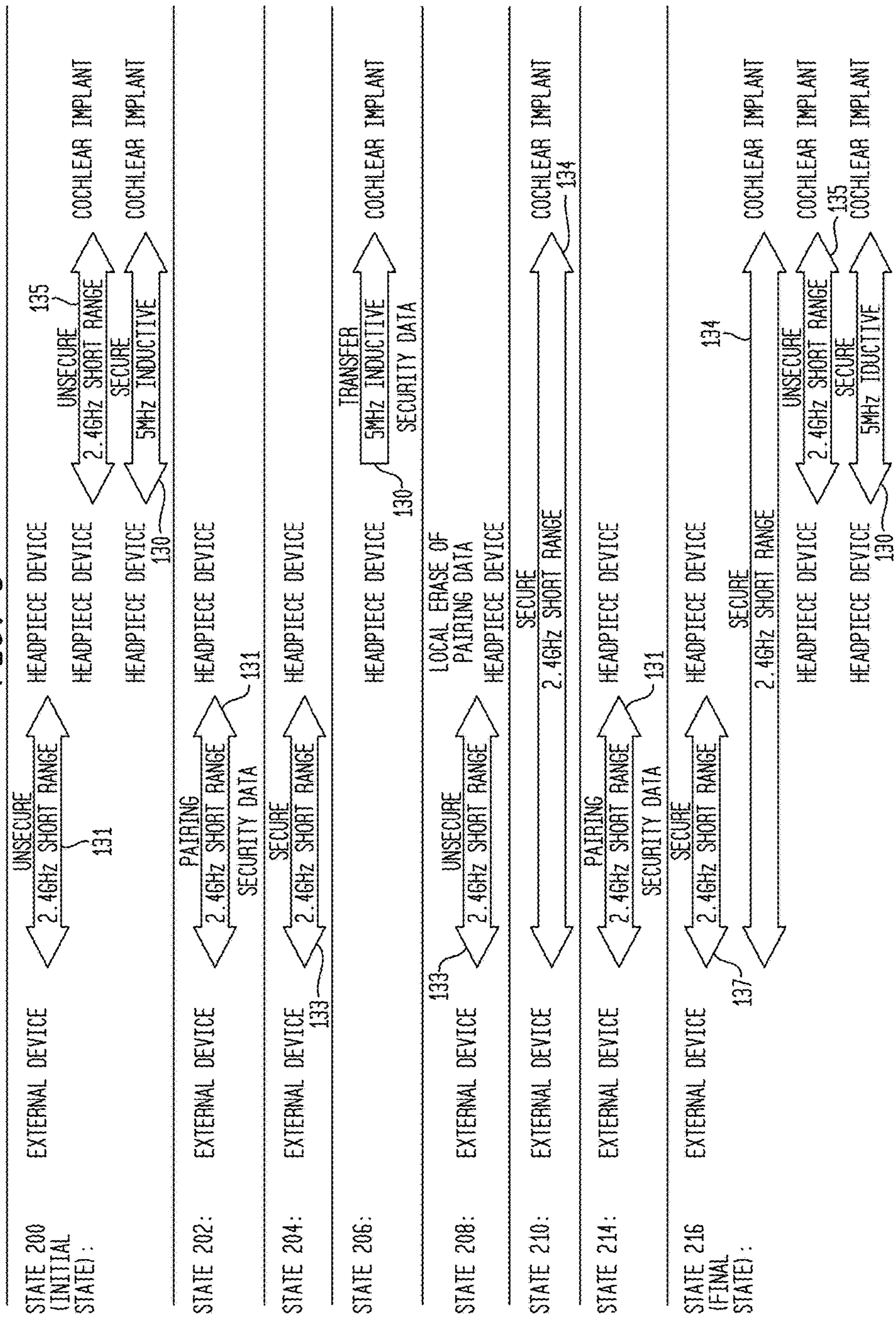
FIG. 6 is another diagram illustrating successive connectivity states for components of a cochlear implant system in accordance with embodiments presented herein.

In the example of FIG. 6, connectivity states 200 through 210 are substantially the same as described above with reference to FIG. 5. However, an additional connectivity state 214 is added and the final state, shown at reference number 216, is different than that shown in FIG. 5.

More specifically, as noted above, in connectivity state 208, the headpiece device 108 locally deletes the security data previously negotiated with external device 106, resulting in the unsecure non-closely coupled wireless connection 131 between the headpiece device and the external device. In the connectivity state 214 of FIG. 6, the external device 106 and headpiece device 108 implement a second or supplemental pairing process to form a supplemental secure non-closely coupled wireless connection 137 between the external device and headpiece device. As a result, as shown in the final connectivity state 216, in the embodiment of FIG. 6, the external device has a direct secure non-closely coupled wireless connection with each of the headpiece device 108 and the cochlear implant 104.

The re-pairing of the external device 106 with the headpiece device 108 to form the secure non-closely coupled wireless connection 137 is enabled by assigning two (2) unique addresses (e.g., two Bluetooth® device addresses) to the headpiece device 108. In conventional wireless arrangements, a device is assigned a single unique address that is used by other devices for communication. However, as noted above, the aspects of the present invention usurp/appropriate the unique address of the headpiece device 108 for use by the cochlear implant 104 to communicate with the external device 106. As such, the headpiece device 108 cannot also use that same address to form a secure connection with the external device 106. Therefore, in accordance with embodiments presented herein, after states 206 and 208 where the headpiece device transfers and locally deletes the original security data, the headpiece device 108 is configured overwrite the original unique address with the second unique address (e.g., overwrite in firmware) or to lock the original unique address (give it an allocated state). The external device 106 and headpiece device 108 may then perform a supplemental pairing processing using the second unique address (i.e., once the first address is passed, the headpiece device would be discoverable using the second address).

The concept of assigning two unique addresses to the same transceiver, and subsequently using both unique addresses for secured communication, is unique to the problem of implantable components and the specific solution of embodiments of the present invention. In particular, the present inventors have recognized that the need for the second addresses arises from the appropriation of the original unique address of the headpiece device 108 for use by the cochlear implant 104.

FIGS. 5 and 6 illustrate that the headpiece device 108 is a "proxy" device because the headpiece device negotiates the security data on behalf of the cochlear implant 104. FIGS. 5 and 6 also illustrated that the headpiece device 108 is always considered, by the cochlear implant 104, to be a "secure" or "trusted" device when communicating over the closely-coupled link due to the required close proximity of the devices during communication. Finally, FIGS. 5 and 6 illustrate that the headpiece device 108 only temporarily operates as a proxy device. That is, the headpiece device 108 is only interposed between the headpiece device and the external device 106 until the direct connection 134 is created, at which time the external device and cochlear implant 104 are able to communicate directly with one another. As such, the headpiece device is referred to herein as a "temporary secure proxy device" that facilitates the authenticated pairing of the cochlear implant 104 with the external device 106.

Certain hearing prosthesis systems are bilateral devices where two implantable components are implanted in a recipient on opposing sides of the head. In certain bilateral systems, the techniques presented herein enable a headpiece device to authenticate both the left and right implantable components. That is, the same headpiece device can be used to establish a secure link between a controller (external device) and both the left and right implantable components.

FIG. 7 is a flowchart of a method 250 in accordance with embodiments presented herein. Method 250 begins at 252 with the generation of a first set of security data for formation of a secure non-closely coupled connection between an external device and an external component of an implantable medical device system. At 254, the first set of security data is transferred to an implantable component of the implantable medical device system. At 256, the implantable component uses the first set of security data to imitate the external component for direct communication with the external device over the secure non-closely coupled connection.

Embodiments have primarily been described herein with reference to a cochlear implant system and a headpiece device operating as a temporary secure proxy device for authenticated pairing between the external device and the implantable component. However, as noted above, embodiments of the present invention may be used in other implantable medical device systems that make use of a different external component other than a headpiece device. In such embodiments, the external component is a device that is coupled/attached to the recipient so as to form a closely coupled link with the implantable component, such as an auditory brainstem stimulator, implantable pacemaker, defibrillator, functional electrical stimulator, pain relief stimulator, visual prosthesis, implantable sensor, and/or other systems having functional implantable components configured to diagnosis, prevent, monitor, treat or manage a disease or injury or symptom thereof, or configured to investigate, replace or modify the anatomy or of a physiological process.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device system, comprising:

an implantable component configured to be implanted in a recipient of the implantable medical device system;

an external device; and an external component configured to be attached to the recipient and configured to operate as a temporary secure proxy device for wireless pairing of the implantable component with the external device, wherein to operate as a temporary secure proxy device for wireless pairing of the external device with the implantable component, the external component is configured to:

implement a pairing process with the external device to obtain security data for formation of a non-closely coupled wireless connection between the external component and the external device, and transfer the security data of the closely coupled wireless connection to the implantable component over a closely-coupled wireless connection formed between the external component and the implantable component.

2. The implantable medical device system of claim 1, wherein the external component is configured to enable authenticated pairing of the implantable component with the external device.

3. The implantable medical device system of claim 1, wherein the implantable component is configured to use the security data to securely spoof the non-closely coupled wireless connection between the external component and the external device.

4. The implantable medical device system of claim 1, wherein after the external component transfers the security data to the implantable component, the external component is configured to locally delete the security data.

5. The implantable medical device system of claim 1, wherein the implantable component is configured to operate as a secure router device enabling secure communication between the external component and the external device.

6. The implantable medical device system of claim 1, wherein the implantable component is a cochlear implant.

7. A method, comprising:

generating a first set of security data for formation of a secure non-closely coupled connection between an external device and an external component of an implantable medical device system;

transferring the first set of security data to an implantable component of the implantable medical device system; and at the implantable component, using the first set of security data to imitate the external component for direct communication with the external device over the secure non-closely coupled connection.

8. The method of claim 7, wherein generating security data for formation of the secure non-closely coupled connection between the external device and the external component comprises:

performing an authenticated pairing process such that the secure non-closely coupled connection includes man-in-the-middle (MITM) protection.

9. The method of claim 7, wherein transferring the first set of security data to an implantable component comprises:

transferring the first set of security data to the implantable component over a closely-coupled wireless connection formed between the external component and the implantable component.

10. The method of claim 9, further comprising:

transferring the first set of security data to the implantable component using a low power communication mode to limit the range of the closely-coupled wireless connection.

11. The method of claim 7, wherein after the external transfers the first set of security data to the implantable component, the method further comprises:

locally deleting the first set of security data at the external component.

12. The method of claim 11, further comprising:

receiving, at the implantable component, data over the secure non-closely coupled connection, wherein the data is directed to the external component;

transferring the data from the implantable component to the external component over a closely-coupled wireless connection formed between the external component and the implantable component.

13. The method of claim 11, wherein after locally deleting the first set of security data at the external component, the method further comprises:

generating a second set of security data for formation of a second secure non-closely coupled connection between the external device and the external component of the implantable medical device system.

14. An implantable medical device system, comprising:

an implantable component configured to be implanted in to a recipient of the implantable medical device system; and an external component having a first unique device address assigned thereto, wherein the external component is configured to:

use the first unique device address to wirelessly pair the external component with an external device and form a non-closely coupled wireless connection between the external component and the external device, and transfer the first address to the implantable component, wherein the implantable component is configured to use the first address to communicate with the external device on the non-closely coupled wireless connection formed between the external component and the external device.

15. The implantable medical device system of claim 14, wherein the external component is configured to transfer the first unique device address to the implantable component over a closely coupled wireless connection formed between the external component and the implantable component.

16. The implantable medical device system of claim 14, wherein the implantable component is configured to use the first address to securely spoof the non-closely coupled wireless connection between the external component and the external device.

17. The implantable medical device system of claim 14, wherein the external component has both the first unique device address and a second unique device address assigned, and wherein after the external component transfers the first address to the implantable component, the external component is configured make the external component discoverable to the external device using the second unique device address.

18. The implantable medical device system of claim 17, wherein the external component is configured to use the second unique address to wirelessly pair the external component with the external device and form a second non-closely coupled wireless connection between the external component and the external device.

19. An implantable medical device system, comprising:

an implantable component configured to be implanted in a recipient of the implantable medical device system;

an external device; and an external component configured to be attached to the recipient and configured to operate as a temporary secure proxy device for wireless pairing of the implantable component with the external device, wherein to operate as a temporary secure proxy device for wireless pairing of the external device with the implantable component, the external component is configured to:

implement a pairing process with the external device to obtain security data for formation of a non-closely coupled wireless connection between the external component and the external device, and transfer the security data of the closely coupled wireless connection to the implantable component, wherein the implantable component is configured to use the security data to securely spoof the non-closely coupled wireless connection between the external component and the external device.

20. The implantable medical device system of claim 19, wherein the external component is configured to enable authenticated pairing of the implantable component with the external device.

21. The implantable medical device system of claim 19, wherein the external component is configured to transfer the security data to the implantable component over a closely-coupled wireless connection formed between the external component and the implantable component.

22. The implantable medical device system of claim 19, wherein after the external component transfers the security data to the implantable component, the external component is configured to locally delete the security data.

23. The implantable medical device system of claim 19, wherein the implantable component is configured to operate as a secure router device enabling secure communication between the external component and the external device.

* * * * *